United States Patent [19]

Edens et al.

[11] Patent Number: 4,761,398

[45] Date of Patent: Aug. 2, 1988

[54] METHOD OF INDUCING BIRDS TO MOLT

[75] Inventors: Frank W. Edens, Raleigh; James P. Thaxton, Apex, both of N.C.

[73] Assignee: Embrex, Inc., Raleigh, N.C.

[21] Appl. No.: 897,749

[22] Filed: Aug. 18, 1986

[51] Int. Cl.$^4$ .................. A61K 37/43; C07K 7/20
[52] U.S. Cl. ........................ 514/15; 514/21; 514/800; 530/313; 424/491
[58] Field of Search ............... 530/313; 514/21, 15, 514/800; 424/491

[56] References Cited

U.S. PATENT DOCUMENTS

| | | | |
|---|---|---|---|
| 3,864,482 | 2/1975 | Naito et al. | 514/15 |
| 4,010,125 | 3/1977 | Schally et al. | 530/313 |
| 4,234,571 | 11/1980 | Nestor et al. | 530/313 |
| 4,318,905 | 3/1982 | Nestor et al. | 514/15 |
| 4,377,515 | 3/1983 | Veber et al. | 530/323 |
| 4,481,190 | 11/1984 | Nestor et al. | 514/16 |

OTHER PUBLICATIONS

Garmatina, *Probl. Fiziol. Gipotalamusa Kiev* (17), pp. 96-101 (1983).
Brian H. Vickery, *Endocrine Reviews* 7, 115 (1986).
A. L. Johnson, *Reproduction in the Female*.
H. R. Wilson, J. L. Fry, R. H. Harms and L. R. Arrington, *Poultry Science* 46, 1406 (1967).
Richard K. Noles, *Poultry Science* 45, 50 (1965).
A. van Tienhoven, The Halpin Lecture, 1980.
A. L. Johnson, Patricia A. Johnson and A. van Tienhoven, *Biology of Reproduction* 31, 646 (1984).
W. H. Burke and E. A. Cogger, *Poultry Science* 56, 234 (1977).
R. J. Etches, J. B. Williams and J. Rzasa, *J. Reprod. Fert.* 70, 121 (1984).
B. G. Novikov, S. M. Garmatina and O. V. Danilova, *Chem. Abstracts* 91:172048s (1979).
A. L. Johnson and A. van Tienhoven, *Chem. Abstracts* 95:55156x (1981).
S. M. Garmatina, *Chem. Abstracts* 100:189230x (1984).

*Primary Examiner*—John Kight
*Assistant Examiner*—Christina Chan
*Attorney, Agent, or Firm*—Bell, Seltzer, Park & Gibson

[57] ABSTRACT

Birds are induced to molt by administering them a LHRH receptor ligand. One preferred ligand for administration is the LHRH agonist [D-Trp$^6$] LHRH. Suitable subjects for treatment are laying hens which are at or near the end of their egg laying cycle, which can be induced to molt and returned to egg production by the method provided.

22 Claims, No Drawings

METHOD OF INDUCING BIRDS TO MOLT

FIELD OF THE INVENTION

This invention involves methods of inducing birds to molt without the necessity of subjecting them to a stressful forced molt procedure. In particular, this invention involves methods of inducing birds to molt by administering them Luteinizing Hormone Releasing Hormone (LHRH) receptor ligands.

BACKGROUND OF THE INVENTION

In the wild, most birds seasonally reduce their rate of egg production, molt, and migrate. Vestiges of this natural cycle remain in domestic fowl: after 50 to 60 weeks of laying eggs, egg production becomes sporadic. Because the key to commercially successful egg production is to obtain consistent rates of egg laying from the hens, it is economically desirable to "force" the hens to molt when their rate of egg production becomes sporadic, and thereafter return them to a profitable level of egg production. Such procedures are generally discussed in Wilson, Fry, Harms and Arrington, *Poultry Science* 46, 1406–12 (1967), and Noles, *Poultry Science* 45, 50–57 (1965).

A combination of feed and water restriction and decreased daylength is commonly employed to induce a forced molt. Numerous experiments on these procedures have been conducted in efforts to improve their usefulness. Nevertheless, significant problems remain: foremost is that present commercial practices employ starvation procedures with an attendant high mortality rate, and these procedures are severely criticized for humanitarian reasons. In addition, such treatments often result in the post-molt production of low quality eggs which are overly large in size and have fragile, poor quality shells. Some egg producers attempt to reduce the high mortality rates which accompany a forced molt by subjecting their birds to less stressful procedures and only partially molting them. However, such incomplete forced molt procedures, sometimes referred to as "forced rest" procedures, result in a short period of post-treatment egg production; thus, economic returns are minimized.

Objects of the present invention are, accordingly, to provide a method of inducing laying hens to molt which does not involve starving or stressing the birds, allows the birds to be returned to efficient egg production, and causes the birds to thereafter produce good quality eggs of a good size, with good quality shells. Additional objects and advantages of our invention are discussed in detail below.

SUMMARY OF THE INVENTION

These and other objects and advantages of the invention are accomplished by the provision of a method of inducing birds to molt. The method comprises administering to the bird a Luteinizing Hormone Releasing Hormone (LHRH) receptor ligand in an amount and for a time effective to cause the bird to drop its feathers. Preferably, the method is used to induce birds to have a substantially complete molt. However, the invention can also be used to induce birds to partially molt, or experience a "forced rest." Thus, the phrase "drop its feathers," when used to describe the present invention, is intended to encompass both the substantial feather drop which accompanies a complete molt, and the partial feather drop which accompanies a partial molt or forced rest.

The present invention may more narrowly be described as a method of inducing a bird which is at or near the end of its reproductive cycle to molt, and thereafter returning the bird to reproductive activity. The method comprises, first, administering to the bird a LHRH receptor ligand in an amount effective to reduce the blood Luteinizing Hormone (LH) level of the bird to a level which is insufficient to maintain gametogenesis, then maintaining a depressed blood LH level in the bird with the LHRH receptor ligand for a time sufficient to cause the bird to drop its feathers, and thereafter permitting the blood LH level of the bird to return to a normal level so that the bird may be returned to reproductive activity.

An improvement of the present invention comprises parenterally depositing a biodegradable polymer within the bird, with the polymer having incorporated therein an amount of the LHRH receptor ligand effective to cause the bird to cease gametogenesis and drop its feathers.

The present invention can be practiced on all types of domestic fowl, including chickens, turkeys, ducks, geese, and commercial game birds. It is preferably practiced on hens, including all types of broiler breeder hens and all types of laying hens, with laying hens derived from Leghorn stock being particularly suitable subjects.

DETAILED DESCRIPTION OF THE INVENTION

Ovulation in hens is triggered by Luteinizing Hormone (LH), which is secreted from the hen's pituitary gland. The release of LH is triggered by a polypeptide called Luteinizing Hormone Releasing Hormone (LHRH), which is synthesized in the hen's brain and secreted directly into the hen's pituitary gland (through a special network of blood vessels called the "hypothalamo-hypophyseal portal system") in a complex and tightly controlled pattern. After release, LHRH binds to LHRH receptors in the hen's pituitary gland and stimulates LH secretion. See generally A. L. Johnson, P. A. Johnson and A. Van Tienhoven, 31 *Biology of Reproduction* 646 (1984).

A. LHRH Receptor Ligands

LHRH receptor ligands are used in the present invention to terminate LH secretion in the hen for a time sufficient to cause the hen to stop laying eggs, involute its reproductive tract, and drop its feathers (to molt). This is accomplished with both LHRH receptor ligands that mimic the effect of LHRH (LHRH "agonists") and with LHRH receptor ligands that block the effect of LHRH (LHRH "antagonists"). LHRH agonists cause this effect by hyperstimulating, and thereby desensitizing, the LHRH receptors in the pituitary (a phenomenon called "downregulation"); LHRH antagonists cause this effect by blocking the LHRH receptors and preventing LHRH itself from exerting its usual effect. LHRH agonists can cause downregulation after a single exposure, while LHRH antagonists must be continually present to prevent LHRH naturally secreted from the subject animal's pituitary ("endogenous"LHRH) from binding to and having its normal effect on the LHRH receptor. LHRH agonists are therefore preferred in practicing the present invention because they can generally be administered to the hen in lower dosages to accomplish the desired effect.

Because of their potential as contraceptive agents in humans, numerous LHRH analogs which are either LHRH agonists or antagonists have been synthesized and investigated. See generally B. H. Vickery, 7 *Endocrine Reviews* 115 (1986); A. V. Schally, 2 *Research Frontiers in Fertility Regulation* 1 (1983). J. H. Nestor, T. L. Ho, R. Tahilramani, G. I. McRea and B. H. Vickery, *Long Acting LHRH Agonists and Antagonists*, in *LHRH and its Analogs*, 24 (F. Zabie, A. Belanger, and A. Dudpont, Eds. (hereinafter "Nestor et al."). An "analog" is a chemical compound similar in structure to another, which has either a similar or opposite physiological action. Such LHRH analogs are useful for practicing the present invention. In retrospect, the knowledge gained from this work on LHRH analogs is invaluable in practicing the present invention. An introduction to this field is set forth below.

As set forth herein and for convenience in describing this invention, the conventional abbreviations for the various common amino acids are used as generally accepted in the art, as recommended by the IUPAC-IUB Commission on Biochemical Nomenclature, *Biochemistry*, 11, 1726 (1972). These abbreviations represent L-amino acids, with the exception of the achiral amino acid glycine. Abbreviations used herein for peptides which do not occur in nature are those generally accepted in the art. All peptide sequences mentioned herein are written according to the generally accepted convention, with the N-terminal amino acid on the left and the C-terminal amino acid on the right.

LHRH Agonists

A major increase in the biological activity of agonistic LHRH analogs was early on found to occur when the glycine in the 6-position of LHRH was replaced by D-Ala, D-Leu, D-Phe, D-Trp, or other D-amino acids. The activities of these D-6 amino acid analogs appear to increase as the size of the side chain increases: this suggests that the hydrophobicity of the analog is a factor in determining its activity. Schally, supra at 3. [D-Trp$^6$]LHRH, one such LHRH analog which shows prolonged activity, and which is a particularly preferred compound for practicing the present invention, is described in U.S. Pat. No. 4,010,125.

Highly active LHRH agonists also have been produced with the incorporation of an ethylamide (EA) in the 10 position and a D-amino acid in the 6-position. Examples of such compounds are [D-Leu$^6$, des Gly$^{10}$]LHRHEA and [D-Ser (BU$^1$)$^6$] LHRHEA. Changes in the 6 and-10 positions can thus reinforce one another to produce highly active agonists. Schally, supra at 4.

The peptide bonds between the 3–4, 5–6, and 9–10 substituents have been suggested to be the primary cleavage sites for the enzymatic degradation of LHRH. In connection with these data, substitutions in the 6 and 10-positions which resist enzymatic degradation have been found to produce potent agonists. For example, a D-amino acid in the 6-position, in conjunction with a Pro$^9$-NHEt substitution in place of the Gly$^{10}$ residue, produces highly potent analogs. The aza-Gly$^{10}$(-NH-NH-CO-NH$_2$) substitution, which is more hydrophobic and enzyme resistant, also produces potent agonists. A specific example of such an agonist is [D-Trp$^6$, Pro$^9$-NHEt]LHRH. Nestor et al, supra at 24.

As noted above, a correlation apparently exists between the hydrophobicity of the 6-substituent and the degree of agonistic activity in LHRH analogs. This correlation was investigated and analyzed by Nestor et al, supra at 24–29. These researchers investigated a number of LHRH analogs having 6-substitutions providing varying degrees of hydrophobicity. These analogs, in order of increasing hydrophobicity, were [D-Tmo$^6$]LHRH (the moderately hydrophobic 3-(3,4,5-trimethoxyphenyl) alanine substituent), [D-Trp$^6$, Pro$^9$-NHEt]LHRH, [D-Cha$^6$]LHRH, [D-Pfp$^6$]LHRH, [D-Nal(1)$^6$]LHRH, [D-Nal(2)$^6$]LHRH (the strongly hydrophobic 3-(2-napthyl) alanine substituent), [D-Mtf$^6$]LHRH, [D-ptf$^6$]LHRH, [D-Tmp$^6$]LHRH (the strongly hydrophobic 3-(2,4,6-trimethylphenyl) alanine substituent), and [D-Dca$^6$]LHRH (the extremely hydrophobic 3-(dicyclo-hexylmethyl) alanine substituent). All were more potent than LHRH, but activity dropped off for the strongly hydrophobic [D-Dca$^6$]LHRH. These and other data indicated that an optimum hydrophobicity point greater than that of [D-Trp$^6$]LHRH for agonistic activity existed. Accordingly, addition of a hydrophobic Pro$^9$-NHEt substitution to the basic [D-Nal(2)$^6$]LHRH structure was found to decrease potency, while addition of the hydrophilic aza-Gly$^{10}$ substituent (also resistant to enzymatic degradation) to the same basic structure was found to increase potency. This [D-Nal(2)$^6$], aza-Gly$^{10}$]LHRH analog is apparently one of the most potent LHRH agonists known.

Illustrative examples of some LHRH receptor agonists which have been studied in detail and which can be used in practicing the present invention are:
LHRH
[D-Ser(tBu)$^6$, Aza-Gly$^{10}$]LHRH;
[D-Trp$^6$]LHRH;
[D-Trp$^6$,Pro$^9$-NHEt]LHRH;
[D-His(Bzl)$^6$, Pro$^9$-NHEt]LHRH;
[D-Nal(2)$^6$]LHRH;
[D-Nal(2)$^6$, Pro9-NHEt]LHRH;
[D-Nal(2)$^6$, Aza-Gly$^{10}$]LHRN;
[D-Leu$^6$,Pro$^9$-NEt]LHRH;
[D-Trp$^6$,NMeLeu$^7$, Pro$^9$-Net]LHRH; and
[D-Ser(tBu)$^6$, Pro$^9$-NEt]LHRH.
Nestor et al, supra at 28; Vickery, supra at 117.

LHRH Antagonists

The first LHRH analog showing significant antagonistic activity was [desHis$^2$, desGly$^{10}$] LHRHEA. It was then found that the 3-position could be substituted to give compounds with some antagonistic activity, such as Leu$^3$-LHRH. Other analogs which were then tested and found to have antagonistic activity were [desHis$^2$, Leu$^3$, desGly$^{10}$] LHRHEA, [desHis$^2$, D-Ala$^6$, desGly$^{10}$] LHRHEA, [desHis$^2$, D-Ala$^6$] LHRH and [desHis$^2$, Leu$^3$, D-Ala$^6$, desGly$^{10}$] LHRHEA. Of these, [desHis$^2$, D-Ala$^6$, desGly$^{10}$] LHRHEA and [desHis$^2$, Leu$^3$, D-Ala$^6$, desGly$^{10}$] LHRHEA showed some agonistic activity. Thus incorporation of either a D-amino acid in the 6-position or a C-terminal ethylamide group improved antagonistic activity, while incorporation of both increased agonistic activity. Substitution of D-leucine or D-phenylalanine into the 6-position to produce analogs such as [desHis$^2$, D-Phe$^6$]LHRH also increased antagonistic activity.

Better antagonists can be produced with the replacement of His in the 2-position, instead of its deletion. Exemplary of these compounds are [D-Phe$^2$, D-Leu$^6$]LHRH; [D-Phe$^2$, D-Phe$^6$]LHRH; [D-Phe$^2$, D-Ala$^6$]LHRH; and [D-Phe$^2$, D-Phe$^6$, aza-Gly$^{10}$]LHRH. In addition, modification of the 3-position also has been fruitful in producing LHRH antagonists. Exemplary of these compounds are [D-Phe$^2$, Phe$^3$, D-Phe$^6$]LHRH; [D-Phe$^2$, D-Trp$^3$, D-Phe$^6$]LHRH; and [D-Phe2, Pro$^3$, D-Trp$^6$]LHRH.

Antagonistic activity also has been increased with the use of a D-Lys substitution at the 6-position, and the use of its E-amino as a branching point. One such branched chain antagonist is [D-Phe$^2$, D-Trp$^3$, N-(pyroGlu-D-Phe-D-Trp-Ser-Tyr)-D-Lys$^6$]LHRH. The increased activity of this compound over its straight chain counterpart is believed due to the two N-termini interacting simultaneously with two receptor sites. In this connection, a peptide with three N-termini has been found to have decreased activity, apparently because of steric hindrance between the chains.

Dimers of D-Phe$^2$, [D-Trp$^3$, D-Lys$^6$]LHRH are also potent antagonists. The best of these compounds are the isophthaloyl and succinoyl dimers, such as the isophthaloyl dimer of [D-pyroGlu,D-Phe$^2$, D-Trp$^3$, D-Lys$^6$]LHRH.

Subsequent research on 1-substitutions revealed that the substitution of acylated D-amino acids produced good antagonists. Exemplary of these compounds is [N-Ac-D-Phe$^1$,D-p-Cl-Phe$^2$,D-Trp$^3$,D-Trp$^6$]LHRH. In addition, replacement of D-Phe with D-p-Cl-Phe in the 1-position has been found to produce an improved antagonist. [Ac-D-Trp$^{1,3}$, D-p-Cl-Phe$^2$,D-Phe$^6$]LHRH also has been found to be an active antagonist. Antagonistic analogs also have been increased in their antagonistic activity by incorporating D-Ala into the 10 position. ExemplarY of these antagonists are [Ac-D-Phe$^1$,D-p-Cl-Phe$^2$, D-Trp$^{3,6}$,D-Ala$^{10}$]LHRH; [Ac-D-p-Cl-Phe$^{1,2}$,Trp$^3$, D-Phe$^6$, D-Ala$^{10}$]LHRH; and [N-Ac-D-Trp$^{1,3}$,D-p-Cl-Phe$^2$,D-Phe$^6$,D-Ala$^{10}$]LHRH.

Other substitutions in the 1-position have also yielded useful antagonists. Exemplary is [Ac-Gly-1-D-p-Cl-Phe$^2$, D-Trp$^{3,6}$]LHRH. The Ac-dehydro-Pro$^1$ substitution in the 1-position combined with the D-p-Cl-Ph substitution in position 2, has produced antagonists such as [Ac-dehydro-Pro$^1$,D-p-Cl-Phe$^2$,D-Trp$^{3,6}$]LHRH. Another highly active antagonist which has beta-(2-Naphthyl-D-Ala) substitutions in positions 3 and 6 is [Ac-dehydro-Pro$^1$-D-p-F-Phe$^2$,beta(2-Naphthyl)-D-Ala$^{3,6}$]LHRH.

Use of a D-lysine, or more preferably D-arginine, in the 6-position of LHRH antagonists apparently produces greater antagonistic activity than in the corresponding D-Phe$^6$ or D-Trp$^6$ analogs. [Ac-D-p-Cl-Phe$^{1,2}$,D-Trp$^3$,D-Arg$^6$,D-Ala$^{10}$]LHRH, for example, is a powerful antagonist. Schally, supra at 5. Further investigations of analogs having D-Arg in the 6-position have yielded a number of potent LHRH antagonists. Nestor, supra at 30. Illustrative examples of some additional LHRH receptor antagonists which have been investigated and can be used in practicing the present invention are:
[N-Ac-D-pCl-Phe$^1$,D-pCl-Phe$^2$,
D-Trp$^2$,D-Arg$^6$,D-Ala$^{10}$]LHRH and
[N-Ac-D-Nal(2)$^1$,DCl-Phe$^2$,
D-Trp$^3$,D-hArg(Et$^2$)$^6$,D-Ala$^{10}$ ]LHRH.
Vickery, supra at 117

Polypeptides useful in practicing the present invention may be synthesized by any of a number of known procedures. A summary of some of these procedures may be found in J. M. Stewart and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1973 for solid phase peptide synthesis, and E. Schroder and K. Lubke, "The Peptides", Vol. 1, Academic Press (New York), 1965 for classical solution synthesis.

The foregoing discussion is intended to provide a general introduction to this area: it is by no means a comprehensive review of the state of the art. Review articles on which the foregoing discussion is based, and which should be referred to to locate numerous references in this area, include Vickery, supra; Schally, supra, and Nestor et al, supra. Representative patent references which pertain to LHRH agonists and antagonists include U.S. Pat. Nos. 4,581,169; 4,530,920; 4,481,190; 4,419,347; 4,377,515; 4,341,767; 4,318,905; and 4,234,571. Applicants specifically intend that these and all other references cited herein be incorporated herein by reference.

LHRH receptor agonists and antagonists can be administered to birds in the form of their pharmaceutically acceptable salts. Pharmaceutically acceptable salts are salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acids, naphthalenedisulfonic acids, polygalacturonic acid, and the like; (b) salts with polyvalent metal cations such as zinc, calcium, bismuth, barium, magnesium, aluminum, copper, cobalt, nickel, cadmium, and the like; or with an organic cation formed from, N, N'-dibenzylethylenediamine or ethylenediamine; or (c) combinations, of (a) and (b), e.g. a zinc tannate salt, and the like.

B. Administration to birds

The compounds described above may be administered to birds in a variety of ways, such as by nasal spray, intramuscular injection, subcutaneous injection and intraperitoneal injection.

When the present invention is practiced by administering LHRH ligands as a nasal spray, the LHRH ligands will preferably be prepared in formulations which will contain surfactants to enhance peptide absorption. For example, incorporation of surfactants such as ethylenediamine salts and bile acids and their salts into nasal formulations in amounts of about 0.02–10%, will enhance the amount of peptide passing through the mucous membrane.

A preferred method of administration for practicing the present invention is to parenterally deposit a depot amount of the LHRH receptor ligand in a single step, as opposed to, for example, a series of daily injections. A "depot amount" herein refers to an amount of the LHRH receptor ligand effective to cause the bird to molt. A depot amount of drug should be deposited into the bird in a manner that will cause the drug to slowly be released into the animal, over a prolonged period of time, to thereby maintain a depressed LH level in the bird being treated for a time sufficient to cause the bird to drop its feathers. Depot amounts can be administered by parenterally implanting within the bird a timed-release depot containing the LHRH receptor ligand. Timed-release depots can be provided in numerous ways, such as by incorporating the LHRH receptor ligands into liposomes, or by incorporating the ligand into various polymers. Another example of depot administration is provided by U.S. Pat. No. 4,256,737. An improved means for administering such a depot amount in practicing the present invention is by parenterally depositing a biodegradable polymer having the LHRH receptor ligand incorporated therein.

Polylactide polymers are a preferred group of biodegradable polymers into which a depot amount of an LHRH receptor ligand can be incorporated. Such polymers, and their use, are disclosed in U.S. Pat. No. 3,773,919, at column 2, lines 1-4, and column 7, line 12 et seq.

In this document the term "polylactide" includes both its generic meaning as a polyester derived from an alpha-hydrocarboxylic acid, and its specific meaning for the polymer derived from lactic acid (alpha-hydroxypropionic acid). Thus the term polylactide, when herein used generically, encompasses lactide/glycolide copolymers. Particularly preferred polylactide polymers are polymers formed of polylactide, polyglycolide, and—most particularly—copolymers thereof. These polymers have long been used to make synthetic resorbable sutures: for this reason a great deal is known about their behavior in vivo, and they are preferred compounds for biodegradable drug delivery systems. Properties of these polymers, and methods of making them, are discussed in D. L. Wise et al., Lactic/Glycolic Acid Polymers, in *Drug Carriers in Biology and Medicine*, Chap. 12, (G. Gregoriadis, Ed. 1979), and in T. R. Tice and D. R. Cowsar, Biodegradable Controlled-Release Parenteral Systems, *Pharmaceutical Technology*, page 26 (Nov. 1984).

Polylactides having a high molecular weight (greater than 10,000 daltons) can form films, and are therefore preferred for practicing the present invention. The specific lactide used, in a poly(lactide-co-glycolide) copolymer or otherwise, can be poly(D-lactide), poly(L-lactide), or racemic poly(D,L-lactide). Generally preferred for drug delivery systems are poly(L-lactide) and poly(D,L-lactide). Most preferred is the more amorphous, better coating, poly(D,L-lactide). Best results with these copolymers are obtained with copolymers ranging in molar composition from about 15 to 85 percent poly(glycolide), with the remainder poly(lactide). The rate of copolymer biodegradation is adjusted by altering the lactide/glycolide ratio, as is known in the art.

The biodegradable polymer having the LHRH ligand incorporated therein may be in any physical form suitable for parenteral deposition. Preferably the polymer serves as a matrix in which the LHRH receptor ligand is distributed. Use of various shapes and compositions of these polymers in controlled-release drug delivery systems is discussed in Wise et al. supra, and T. R. Tice and D. R. Cowsar, supra. It is preferred to shape the polymer into small microcapsules having diameters of 250 micrometers or less (sometimes also referred to as "microparticles" or "microspheres"), which can be parenterally injected into the bird through a standard hypodermic syringe. Of course, the polymer can be formed into any shape which can be easily injected into or parenterally deposited within the hen, depending on the equipment available to the user.

Microcapsules useful for practicing the present invention may be prepared by any of a number of known techniques. Like most pharmaceutical treatments, better results will be obtained if the microcapsules are prepared so that the compound incorporated therein will be uniformly and consistently released over time (referred to as "zero-order" release rates). The disclosures of U.S. Pat. Nos. 4,568,559 and 4,389,330 provide excellent instructions on preparing microcapsules of a type useful for practicing the present invention.

The precise amounts in which specific LHRH agonists and antagonists should be administered will depend on factors such as the individual compound's biological (in vivo) half life and affinity for the LHRH receptor, with higher dosages being necessary when compounds having lower binding affinities and/or shorter half lives are used. To keep the dosages at lower levels, compounds having binding affinities for the LHRH receptor, and in vivo half lives, at least as great as LHRH itself are preferred. Precise dosages can be verified by administering the particular compound selected to a laying hen and observing whether the hen stops laying eggs. An alternative verification procedure is to administer the compound to a laying hen and check the hen for a decrease in circulating LH levels by radioimmunoassay. If the blood LH level of the hen goes to a level which is insufficient to maintain the hen's reproductive tract, a treatment which will maintain such a depressed blood LH level for a period of about 10 days will cause the hen to molt. Such a radioimmunoassay procedure is preferable to the egg-laying assay described above, because an interruption in egg laying can be caused by a general toxic effect of the compound being administered.

C. Examples of the invention

To demonstrate the present invention, a carefully controlled experiment was conducted with 296 single combed White Leghorn hens which had been laying eggs under commercial conditions for the previous 47 weeks.

Pre-Molt Period

During the experiment, two birds were assigned to each cage ($12'' \times 18''$). The hens were maintained in their cages for two weeks prior to the molt. They received a 17 hour light: 7 hour dark photoperiod throughout this phase of the experiment. During this time, the following parameters were measured:(a) body weight (weekly); (b) feed consumption (all hens received a common layer ration, and the feed consumed during this two week period was measured); (C) production records (daily); and (d), total egg weight, egg shell weight, and egg specific gravity (measured on three consecutive days each week). Serum samples were taken once, from 10 randomly selected hens from each treatment group, and saved for future study.

Molting period

After the two week pre-molt adjustment period, the hens were randomly assigned to each of eight different groups. These treatment groups were as follows: (1) control, (2) forced molt, (3) chemical molt-injected, (4) vehicle control-injected, (5) chemical molt-microcapsules A, (6) vehicle control-microcapsules A, (7) chemical molt-microcapsules B, and (8) vehicle control-microcapsules B.

The hens then received a seven day pre-molt treatment of a 24 hour light, zero hour dark photoperiod. On day 14 of the experiment the photoperiod was then reduced to natural day length for all treatments. Feed was made available ad libitum for all groups except the forced molt group. The forced molt group was deprived of food, but not of water, until a 30% body weight loss occurred (10 days of fasting).

[D-Trp$^6$]LHRH was used as the LHRH receptor ligand for the chemical molt groups. The "chemical molt-injected" group received intramuscular (breast) injections of 25 micrograms/day of [D-Trp$^6$]LHRH for 10 consecutive days beginning on day 14. Alternate pectoral (breast) areas were injected each day. The "chemical molt-microcapsule" groups received a single intramuscular (breast) injection of microencapsulated [D-Trp$^6$]LHRH on day zero. This preparation of microcapsules provided a controlled release of 25 micrograms [D-Trp$^6$]LHRH per day for 15 consecutive days.

For all treatments, body weights were measured at day zero and every three days thereafter, until the forced molt group achieved a 30% weight loss. Serum samples were periodically collected from 10 hens randomly selected from each group, and saved for future analysis. The same 10 hens from each group were bled at each collection.

On day 14, the microcapsule injected groups received intramuscular injections of lactide/glycolide copolymer microcapsules which had [D-Trp$^6$]LHRH incorporated therein. The ligand-containing microcapsules administered the "Microcapsules A" group were prepared and supplied by Debiopharm (Lausanne, Switzerland). These microcapsules were prepared by a phase-separation process to produce a free-flowing powder of spherical particles consisting of [D-Trp$^6$]LHRH (2% wt/wt) distributed within a polymeric matrix of 53:47(mol %) poly(DL-lactide-co-glycolide) (98% wt/wt) with an inherent viscosity of 0.7 dl/g. The microcapsules were 50 micrometers or less in diameter. The surfaces of the microspheres were smooth, indicating that a continuous coating of polymer was present. Photomicrographs of similar microcapsules are presented in T. W. Redding, et al., *Proc. Natl. Acad. Sci. U.S.A.*, 81, 5845 (Sept. 1984).

Microcapsules were suspended in disposable syringes in vehicle containing 2% carboxymethyl cellulose and 1% "TWEEN 20" in water. After thoroughly mixing the suspension, aliquots calculated to have released a dose of 25 micrograms/day for 15 consecutive days were injected into the breast muscle of the hens. We weighed the microcapsules directly into disposable 3 ml syringes. The plunger of a plugged syringe containing microcapsules (without vehicle) was pulled back to the 1.5-2 cc mark. The hub of the syringe was then placed against a vortex mixer and the syringe vortexed rapidly for about 20 seconds, or until most of the clumps of microbeads were broken and distributed along the barrel of the syringe. An 18 gauge needle was then attached and 0.7 to 1.0 ml of polyvinyl pyrollidone injection vehicle was drawn into the syringe. With the needle in an upward position, the syringe was again placed against a vortex mixer and vortexed rapidly for 20 seconds, or until a suspension of microbeads was formed in the vehicle. Holding the syringe with the needle in an upward position, air and bubbles were gently forced out and the microcapsules quickly injected deep into the breast muscle of the hen being treated. (This procedure can be a little difficult for those who have not worked with microcapsules before).

Post-molt recovery period (approximate length: 14 days)

After the forced molt group achieved a 30% body weight loss, i.e., after 10 days of fasting, six hens from each group were necropsied. The liver, abdominal adipose tissue (fat pad), ovary plus ova and oviduct weights were measured. The remaining forced molt hens received a limited quantity of feed for two days, and were then fed ad libitum. For all groups, body weight and feed consumption were measured weekly. The lighting regime was increased, at weekly intervals, from natural day length to 17 hour light: seven hour dark. For the forced molt and chemical molt groups, when the first egg was produced after the molt, body weights were measured and body weights taken for the 10 selected birds.

Production Period

The remaining hens were maintained for a three month production period, during which the following parameters were measured: a. body weight (weekly for the first month and then twice a month); b. feed consumption (measured weekly); c. egg production (measured daily); and d. egg weight, shell weight and specific gravity (measured for three consecutive days each week for the first month, and then three consecutive days every two weeks).

Results and Discussion

The following tables present the data collected from the procedures described above. Table 1 shows the weights of the hens in the various groups throughout the molt and in the production stage thereafter. Table 2 presents the egg production data, and Table 3 presents the feed consumption data. Table 4 presents mortality data, and Tables 5-7 present egg parameter data. Table 8 presents the mean body parameters of the six hens in each group killed immediately after the molt.

All groups which were treated with [D-Trp$_6$]LHRH were induced to molt. The "chemical molt-microcapsules B" group did not provide as good a molt, and as good subsequent egg production, as either the "chemical molt-injected" or the "chemical molt-microcapsules A" group. This difference is attributed to a less uniform release rate of the [D-Trp$^6$] LHRH from the "B" microcapsules. Such a partial molt, or forced rest, is useful, but is not as preferable as a more complete molt. This is particularly true with the present invention, where, as explained below, mortality is not a significant concern. For clarity of presentation, data from this group, and its vehicle control, has been omitted from the tables below.

The only significant weight loss in hens treated with [D-Trp$^6$] LHRH can be attributed to the involution of their reproductive tracts [See Table 1 in conjunction with Table 8]. Table 2 shows that both [D-Trp$^6$] LHRH treated groups exhibited involution of their reproductive tracts and then were induced to molt, following which they produced eggs at an efficient rate. Table 3 shows that both [D-Trp$^6$] LHRH groups advantageously did not consume as much feed after the molt as the Forced Molt Group. Specifically, the force molted hens which experienced a 30% loss of body weight subsequently had to regain this weight prior to initiation of post-molt egg production. In order to accomplish this weight gain, the hens ate significantly more feed than the hens molted by administration of [D-Trp$^6$] LHRH, because these hens did not experience a corresponding weight loss. Tables 5, 6 and 7, taken together, show that the eggs produced by the [D-Trp$^6$] LHRH treated groups were as good in quality as the eggs produced by the conventional Forced Molted Group. Egg size, weight, shell weights and specific gravities were comparable in all the molted groups. Table 4 demonstrates a low mortality rate in the [D-Trp$^6$] LHRH treated groups. In fact, no mortality occurred in groups that received [D-Trp$^6$] LHRH and among the treated groups mortality was highest in the Forced Molted Group.

TABLE 1

MEAN BODY WEIGHT (Kg)
TREATMENT[1]

| Day | Control | Forced Molt | Daily Injected D-Trp[6]—LHRH | Daily Injected Control | D-Trp[6]—LHRH Microcapsules[2] | Microcapsule Control |
|---|---|---|---|---|---|---|
| Zero | 1.730 | 1.717 | 1.720 | 1.731 | 1.711 | 1.653 |
| 5 | 1.664 | 1.658 | 1.669 | 1.656 | 1.677 | 1.612 |
| 12[3] | 1.709 | 1.697 | 1.722 | 1.750 | 1.710 | 1.651 |
| 17 | 1.769[4] | 1.384$^B$ | 1.765$^A$ | 1.784$^A$ | 1.758$^A$ | 1.725$^A$ |
| 22 | 1.709$^{AB}$ | 1.206$^C$ | 1.704$^{AB}$ | 1.778$^A$ | 1.689$^B$ | 1.711$^{AB}$ |
| 27 | 1.744$^{AB}$ | 1.576$^D$ | 1.637$^C$ | 1.783$^{AB}$ | 1.587$^D$ | 1.704$^{BC}$ |
| 33 | 1.780$^{AB}$ | 1.694$^D$ | 1.654$^{DE}$ | 1.818$^A$ | 1.613$^E$ | 1.754$^{BC}$ |
| 40 | 1.798 | 1.822 | 1.747 | 1.827 | 1.734 | 1.775 |
| 47 | 1.777 | 1.841 | 1.760 | 1.808 | 1.777 | 1.694 |
| 54 | 1.791 | 1.834 | 1.761 | 1.841 | 1.806 | 1.774 |
| 61 | 1.806 | 1.860 | 1.802 | 1.823 | 1.823 | 1.759 |
| 75 | 1.828 | 1.893 | 1.838 | 1.847 | 1.847 | 1.798 |

[1] For all treatments n = 36 until day 23 and thereafter n = 30.
[2] Debiopharm was the microcapsule source.
[3] On day 13, feed was removed from the Forced Molted treatment and Daily Injections - LHRH and Control were started. On day 14, the microcapsule groups received a single injection.
[4] Means in rows for each variable with different superscripts are significantly different (P is less than .05).

TABLE 2

HEN-DAY EGG PRODUCTION (%) Reported By Weeks
TREATMENT[1]

| Day | Control | Forced Molt | Daily Injected D-Trp[6]—LHRH | Daily Injected Control | D-Trp[6]—LHRH Microcapsules[2] | Microcapsule Control |
|---|---|---|---|---|---|---|
| Zero | 49.206$^{B4}$ | 53.571$^B$ | 63.889$^A$ | 53.968$^B$ | 57.143$^{AB}$ | 53.175$^B$ |
| 5 | 49.206$^{CD}$ | 55.952$^{BC}$ | 61.508$^{AB}$ | 57.937$^B$ | 53.968$^{BC}$ | 45.238$^D$ |
| 12[3] | 50.794$^B$ | 14.286$^D$ | 26.984$^C$ | 59.163$^B$ | 13.492$^D$ | 49.603$^B$ |
| 17 | 60.303$^{BC}$ | 0.0$^D$ | 4.683$^D$ | 67.472$^{AB}$ | 0.794$^D$ | 55.714$^C$ |
| 22 | 61.746$^B$ | 0.0$^E$ | 7.619$^D$ | 72.116$^A$ | 0.0$^E$ | 57.619$^B$ |
| 27 | 65.979$^{BC}$ | 27.513$^D$ | 30.000$^D$ | 74.391$^{AB}$ | 10.000$^E$ | 58.571$^C$ |
| 33 | 70.952$^{AB}$ | 66.865$^{ABC}$ | 58.095$^{CD}$ | 75.185$^A$ | 46.667$^{DE}$ | 65.185$^{BCD}$ |
| 40 | 65.926$^{BCD}$ | 71.098$^{ABC}$ | 63.333$^{CD}$ | 76.984$^A$ | 60.000$^D$ | 74.021$^{AB}$ |
| 47 | 67.725$^C$ | 80.159$^A$ | 67.143$^C$ | 71.005$^{BC}$ | 68.571$^{BC}$ | 73.227$^{ABC}$ |
| 54 | 70.370$^{BC}$ | 78.505$^{AB}$ | 76.667$^{AB}$ | 72.804$^{ABC}$ | 79.524$^A$ | 71.323$^{ABC}$ |
| 61 | 66.138$^B$ | 81.415$^A$ | 80.000$^A$ | 75.079$^A$ | 78.571$^A$ | 73.651$^{AB}$ |
| 75 | 70.304$^{BCD}$ | 88.955$^A$ | 76.667$^B$ | 63.968$^D$ | 72.381$^{BC}$ | 66.190$^{CD}$ |
| 82 | 76.852$^{AB}$ | 79.784$^{AB}$ | 73.889$^{AB}$ | 64.753$^C$ | 82.222$^A$ | 72.963$^{BC}$ |

[1] For all treatments n = 36 until day 23 and thereafter n = 30.
[2] Debiopharm was the microcapsule source.
[3] Weekly analysis began on day zero and ended on day 90; the Forced Molt began during Week 2 on day 13.
[4] Means in rows for each variable with different superscripts are significantly different (P is less than .05).

TABLE 3

FEED CONSUMPTION (grams/hen/day)
TREATMENT[1]

| Day | Control | Forced Molt | Daily Injected D-Trp[6]—LHRH | Daily Injected Control | D-Trp[6]—LHRH Microcapsules[2] | Microcapsule Control |
|---|---|---|---|---|---|---|
| 5–14 | 143.000 | 158.333 | 149.667 | 156.000 | 152.000 | 143.667 |
| 14–22 | 130.667 | 0.0 | 109.000 | 137.000 | 114.000 | 139.333 |
| 22–29 | 140.667$^{A4}$ | 160.667$^A$ | 98.333$^B$ | 144.333$^A$ | 80.000$^B$ | 138.333$^A$ |
| 29–33 | 132.000$^{AB}$ | 155.333$^A$ | 118.000$^{BC}$ | 134.333$^A$ | 102.333$^C$ | 135.333$^{AB}$ |
| 33–40 | 113.667$^A$ | 114.333$^A$ | 105.000$^{AB}$ | 114.667$^A$ | 110.667$^A$ | 113.667$^A$ |
| 40–47 | 122.667$^{AB}$ | 130.000$^A$ | 122.000$^{AB}$ | 129.667$^A$ | 117.000$^{AB}$ | 126.667$^A$ |
| 47–54 | 129.000 | 131.667 | 120.667 | 131.667 | 127.000 | 132.333 |
| 54–61 | 124.333 | 135.667 | 136.667 | 125.667 | 128.333 | 127.000 |
| 61–68 | 129.333 | 136.333 | 133.000 | 120.333 | 127.667 | 129.667 |
| 68–75 | 114.333 | 124.333 | 128.667 | 118.667 | 120.667 | 122.000 |

[1] For all treatments n = 36 until day 23, and thereafter n = 30.
[2] Debiopharm was the microcapsule source.
[3] On day 13, feed was removed from the Forced Molted treatment and Daily Injections - LHRH and Control were started. On day 14, the microcapsule groups received a single injection.
[4] Means in rows for each variable with different superscripts are significantly different (P is less than .05).

TABLE 4

| Treatment | MORTALITY[1] Number of Hens That Died |
|---|---|
| Control | 5 |
| Forced Molt | 4 |
| Daily Injected - D-Trp[6]—LHRH | 0 |
| Daily Injected - Control | 2 |
| D-Trp[6]—LHRH Microcapsules[2] | 0 |

TABLE 4-continued

MORTALITY[1]

| Treatment | Number of Hens That Died |
|---|---|
| Microcapsule Control | 2 |

[1]Evaluated from day 28 to day 94
[2]Debiopharm was the microcapsule source.

TABLE 5

EGG SPECIFIC GRAVITY (g/cm)³
TREATMENT

| Weeks[2] | Control | Forced Molt | Daily Injected D-Trp⁶—LHRH | Daily Injected Control | D-Trp⁶—LHRH Microcapsules[1] | Microcapsule Control |
|---|---|---|---|---|---|---|
| 1 | 1.079 | 1.081 | 1.079 | 1.081 | 1.079 | 1.078 |
| 2 | 1.078 | 1.081 | 1.082 | 1.082 | 1.080 | 1.079 |
| 3 | 1.074 | 1.078 | 1.075 | 1.075 | 1.074 | 1.074 |
| 4 | $1.078^{CD3}$ | $1.081^A$ | $1.079^B$ | $1.078^B$ | $1.079^B$ | $1.077^D$ |
| 5 | $1.074^{DE}$ | $1.080^A$ | $1.079^{AB}$ | $1.076^C$ | $1.077^C$ | $1.076^{CD}$ |
| 6 | $1.076^C$ | $1.080^A$ | $1.080^A$ | $1.075^C$ | $1.07^A$ | $1.076^C$ |
| 7 | $1.075^B$ | $1.079^B$ | $1.079^A$ | $1.074^B$ | $1.08^A$ | $1.075^B$ |

[1]Debiopharm was the microcapsule source.
[2]Specific Gravities were measured each week. The dates for the weeks were:
Week 1 = days zero-2
Week 2 = days 6-8
Week 3 = days 40-42
Week 4 = days 47-49
Week 5 = days 54-56
Week 6 = days 61-63
Week 7 = days 75-77
[3]Means in rows for each variable with different superscripts are significantly different (P is less than .05).

TABLE 6

TOTAL EGG WEIGHT (g)
TREATMENT

| Weeks[2] | Control | Forced Molt | Daily Injected D-Trp⁶—LHRH | Daily Injected Control | D-Trp⁶—LHRH Microcapsules[1] | Microcapsule Control |
|---|---|---|---|---|---|---|
| 1 | 65.44 | 66.09 | 66.04 | 67.19 | 66.88 | 68.99 |
| 2 | 66.60 | 66.70 | 67.72 | 66.99 | 67.99 | 69.48 |
| 3 | 66.36 | 66.83 | 64.38 | 68.11 | 64.85 | 67.27 |
| 4 | 66.69 | 69.78 | 68.27 | 66.97 | 69.06 | 67.35 |
| 5 | 66.84 | 68.64 | 68.81 | 68.67 | 67.24 | 69.62 |
| 6 | 66.60 | 68.70 | 67.4 | 68.26 | 67.24 | 68.34 |
| 7 | 67.66 | 69.18 | 67.19 | 66.31 | 68.42 | 67.81 |

[1]Debiopharm was the microcapsule source.
[2]Egg Weights were measured each week. The dates for the weeks were:
Week 1 = days zero-2
Week 2 = days 6-8
Week 3 = days 40-42
Week 4 = days 47-49
Week 5 = days 54-56
Week 6 = days 61-63
Week 7 = days 75-77

TABLE 7

EGG SHELL WEIGHT (g)
TREATMENT

| Weeks[2] | Control | Forced Molt | Daily Injected D-Trp⁶—LHRH | Daily Injected Control | D-Trp⁶—LHRH Microcapsules[1] | Microcapsule Control |
|---|---|---|---|---|---|---|
| 1 | 5.43 | 5.55 | 5.46 | 5.59 | 5.52 | 5.54 |
| 2 | 5.46 | 5.71 | 5.82 | 5.71 | 5.60 | 5.70 |
| 3 | 5.42 | 5.59 | 5.15 | 5.56 | 5.16 | 5.45 |
| 4 | $5.51^{AB3}$ | $5.90^A$ | $5.61^{AB}$ | $5.48^{AB}$ | $5.68^{AB}$ | $5.38^{AB}$ |
| 5 | 5.53 | 5.96 | 5.79 | 5.73 | 5.68 | 5.79 |
| 6 | $5.38^{CD}$ | $5.88^A$ | $5.65^B$ | $5.55^{BC}$ | $5.65^B$ | $5.58^B$ |
| 7 | $5.41^C$ | $5.72^{AB}$ | $5.59^B$ | $5.37^C$ | $5.65^B$ | $5.38^C$ |

[1]Debiopharm was the microcapsule source.
[2]Shell Weights were measured each week. The dates for the weeks were:
Week 1 = days zero-2
Week 2 = days 6-8
Week 3 = days 40-42
Week 4 = days 47-49
Week 5 = days 54-56
Week 6 = days 61-63
Week 7 = days 75-77
[3]Means in rows for each variable with different superscripts are significantly different (P is less than .05).

TABLE 8

MEAN BODY PARAMETERS OF HENS KILLED IMMEDIATELY AFTER THE MOLT[1] (Means) TREATMENT

| | Control | Forced Molt | Daily Injected D-Trp[6]—LHRH | Daily Injected Control | D-Trp[6]—LHRH Microcapsules[2] | Microcapsule Control |
|---|---|---|---|---|---|---|
| Body Wt. (Kg) | $1.782^{AB3}$ | $1.166^C$ | $1.784^{AB}$ | $1.814^{AB}$ | $1.560^B$ | $1.735^{AB}$ |
| Ovary Wt. (g) | $59.09^A$ | $5.36^B$ | $10.38^B$ | $50.14^A$ | $4.45^B$ | $45.13^A$ |
| Oviduct Wt. (g) | $84.69^A$ | $12.71^B$ | $17.65^B$ | $85.26^A$ | $11.10^B$ | $75.50^A$ |
| Abdominal Adipose Tissue Wt. (g) | $39.78^{AB}$ | $12.15^B$ | $55.73^A$ | $30.52^{AB}$ | $50.79^A$ | $43.55^A$ |

[1]Day 23.
[2]Debiopharm was the microcapsule source.
[3]Means in rows for each variable with different superscripts are significantly different (P is less than .05).

The invention has been discussed with a degree of specificity above. This discussion has been provided for illustrative purposes only, with the scope of the invention being defined by the following claims.

That which is claimed is:

1. A method of inducing an egg laying hen to molt, comprising administering to said egg laying hen a Luteinizing Hormone Releasing Hormone (LHRH) receptor ligand in an amount and for a time effective to cause the hen to stop laying eggs and drop its feathers.

2. A method according to claim 1, wherein said LHRH receptor ligand is selected from the group consisting of LHRH, LHRH analogs, and pharmaceutically acceptable salts thereof.

3. A method according to claim 2, wherein said LHRH ligand is a LHRH agonist.

4. A method according to claim 3, wherein said LHRH agonist is selected from the group consisting of:
LHRH
[D-Ser(tBu)[6],Aza-Gly[10]]LHRH;
[D-Trp[6]]LHRH;
[D-Trp[6],Pro[9]-NHEt]LHRH;
[D-His(Bzl)[6],Pro[9]-NHEt]LHRH;
[D-Nal(2)[6]]LHRH;
[D-Nal(2)[6],Pro[9]-NHEt]LHRH;
[D-Nal(2)[6],Aza-Gly[10]]LHRH;
[D-Leu[6],Pro[9]NEt]LHRH;
[D-Trp[6],NMeLeu[7],Pro[9]NEt]LHRH;
[D-Ser(tBu)[6],Pro[9]NEt]LHRH;
and pharmaceutically acceptable salts thereof.

5. A method according to claim 4, wherein said LHRH agonist is [D-Trp[6]] LHRH or a pharmaceutically acceptable salt thereof.

6. A method according to claim 2, wherein said LHRH receptor ligand is a LHRH antagonist.

7. A method according to claim 6, wherein said LHRH receptor antagonist is selected from the group consisting of:
[N-Ac-D-pCl-Phe[1],D-pCl-Phe[2],
D-Trp[2],D-Arg[6],D-Ala[10]] LHRH;
[N-Ac-D-Nal(2)[1],D-pCl-Phe[2]
D-Trp[3],D-hArg(Et₂)[6],D-Ala[10]] LHRH;
and pharmaceutically acceptable salts thereof.

8. A method of inducing a bird which is at or near the end of its reproductive cycle to molt without the need for depriving the bird of food, and thereafter returning the bird to reproductive activity, said method comprising (i) administering to the bird a Luteinizing Hormone Releasing Hormone (LHRH) receptor ligand in an amount effective to reduce the blood Luteinizing Hormone (LH) level of the bird to a level which is insufficient to maintain gametogenesis; (ii) maintaining a depressed blood LH level in said bird with said LHRH receptor ligand for a time sufficient to cause the bird to drop its feathers, and (iii) thereafter permitting the blood LH level of the bird to return to a normal level so that the bird may be returned to reproductive activity.

9. A method according to claim 8, wherein said LHRH receptor ligand is administered by parenterally implanting within said bird a timed-release depot containing said LHRH receptor ligand.

10. A method according to claim 9, wherein the LH levels in said bird are maintained at said depressed level for a period on the order of about ten days.

11. A method of inducing an egg laying hen to molt, comprising administering to said egg laying hen a Luteinizing Hormone Releasing Hormone (LHRH) receptor ligand selected from the group consisting of LHRH, LHRH analogs, and pharmaceutically acceptable salts thereof, said LHRH receptor ligand being administering by parenterally depositing a polylactide polymer within said hen, said polymer having incorporated therein an amount of said LHRH receptor ligand effective to cause the hen to stop laying eggs and drop its feathers.

12. A method according to claim 11, wherein said LHRH receptor ligand is selected from the group consisting of
LHRH
[D-Ser(tBu)[6],Aza-Gly[10]] LHRH;
[D-Trp[6]] LHRH;
[D-Trp[6],Pro[9]-NHEt] LHRH;
[D-His(Bzl)[6],Pro[9]-NHEt] LHRH;
[D-Nal(2)[6]] LHRH;
[D-Nal(2)[6],Pro[9]-NHEt] LHRH;
[D-Nal(2)[6],Aza-Gly[10]] LHRH;
[D-Leu[6], Pro[9] NEt] LHRH;
[D-Trp[6],NMeLeu[7],Pro[9]NEt] LHRH;
[D-Ser(tBu)[6],Pro[9]NEt] LHRH;
and pharmaceutically acceptable salts thereof.

13. A method according to claim 11, wherein said LHRH receptor ligand is [D-Trp[6]] LHRH or a pharmaceutically acceptable salt thereof.

14. A method according to claim 11, wherein said biodegradable polymer is a lactide glycolide copolymer.

15. A method according to claim 14, wherein said coppolymer contains from about 15 to 85 mol percent lactide.

16. A method of inducing an egg laying Leghorn hen which is at or near the end of its laying cycle to molt without the necessity of depriving the hen of food, comprising administering to said egg laying Leghorn hen a Luteinizing Hormone Releasing Hormone (LHRH) agonist selected from the class consisting of LHRH, LHRH analogs, and pharmaceutically acceptable salts thereof, said LHRH agonist being administered in an amount and for a time effective to cause the hen to stop laying eggs and drop its feathers.

17. A method according to claim 16, wherein said LHRH agonist is administered by the intramuscular injection of a polylactide polymer having said LHRH agonist incorporated therein.

18. A method according to claim 17, wherein said polylactide polymer is a lactide/glycolide copolymer.

19. A method according to claim 18, wherein said copolymer contains from about 15 to 85 mol percent lactide.

20. A method according to claim 17, wherein said polylactide polymer is in the form of injectable microcapsules, said microcapsules having a diameter of about 250 micrometers or less.

21. A method according to claim 20, wherein said polylactide polymer serves as a matrix having said LHRH agonist dispersed therein.

22. A method according to claim 21, wherein said LHRH agonist is selected from the group consisting of:
LHRH
[D-Ser(tBu)$^6$,Aza-Gly$^{10}$]LHRH;
[D-Trp$^6$]LHRH;
[D-Trp$^6$,Pro$^9$-NHEt]LHRH;
[D-His(Bzl)$^6$,Pro$^9$-NHEt]LHRH;
[D-Nal(2)$^6$]LHRH;
[D-Nal(2)$^6$,Pro$^9$-NHEt]LHRH;
[D-Nal(2)$^6$,Aza-Gly$^{10}$]LHRH;
[D-Leu$^6$,Pro$^9$ NEt]LHRH
[D-Trp$^6$,NMeLeu$^7$,Pro$^9$NEt]LHRH;
[D-Ser(tBu)$^6$,Pro$^9$NEt] LHRH;
and pharmaceutically acceptable salts thereof.

* * * * *